(12) United States Patent
Bianco et al.

(10) Patent No.: US 9,402,603 B2
(45) Date of Patent: Aug. 2, 2016

(54) USE OF PULMONARY SURFACTANTS IN LUNG TRANSPLANTATION AND METHODS THEREOF

(71) Applicant: CHIESI FARMACEUTICI S.p.A., Parma (IT)

(72) Inventors: Federico Bianco, Parma (IT); Roberta Razzetti, Parma (IT); Patrizio Vitulo, Parma (IT); Alessandro Bertani, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 13/736,132

(22) Filed: Jan. 8, 2013

(65) Prior Publication Data

US 2014/0128846 A1    May 8, 2014

Related U.S. Application Data

(60) Provisional application No. 61/722,984, filed on Nov. 6, 2012.

(51) Int. Cl.

| | |
|---|---|
| *A61M 37/00* | (2006.01) |
| *A61B 17/00* | (2006.01) |
| *A61B 16/00* | (2006.01) |
| *A61B 5/00* | (2006.01) |
| *A61K 38/00* | (2006.01) |

(52) U.S. Cl.
CPC ............ *A61B 17/00* (2013.01); *A61B 16/00* (2013.01); *A61B 5/413* (2013.01); *A61B 2017/00969* (2013.01); *A61K 38/00* (2013.01)

(58) Field of Classification Search
CPC ..... A01N 1/02; A01N 1/0226; A01N 1/0247; A01N 1/0221; A01N 1/0205; A61M 37/00
See application file for complete search history.

(56) References Cited

U.S. PATENT DOCUMENTS

2011/0136096 A1*    6/2011    Hassanein et al. ............. 435/1.2

FOREIGN PATENT DOCUMENTS

WO    WO 2008/154151    * 12/2008 ............. A61K 38/17

OTHER PUBLICATIONS

Burker et al., Quality of life in patients awaiting lung transplant: Cystic Fibrosis versus other end-stage lung diseases, Pediatric Pulmonology, 30:453-460 (2000).*
Inci et al., Ex Vivo Reconditioning of Marginal Donor Lungs Injured by Acid Aspiration, The Journal of Heart and Lung Transplantation, vol. 27, No. 11, Nov. 2008.*
Trulock, Lung Transplantation for α1-Antitrypsin Deficiency Emphysema, Chest, (Dec. 1996), vol. 110, No. 6, pp. 284S-294S.*
Lordan et al., Pulmonary Arterial Hypertension and Lung Transplantation, Expert Rev Resp Med., (Jun. 2011), vol. 5, No. 3, pp. 441-454.*
Wittwer et al., Impact of exogenenic surfactant therapy as an adjunct for modern lung preservation, The Thoracic and Cardiovascular Surgeon, (2008), 56, Suppl. 1: S23-S130.*
Bertani et al., The Administration of Exogenous Surfactant during Cold Preservation Can Improve Pulmonary Function after Lung Transplantation in a Swine Model of Prolonged Ischemia, The Journal of heart and lung transplantation, vol. 31, Issue 4 (Apr. 2012), p. S221.*
T. N. Machuca, et al., Advances in Lung Preservation, *Surg. Clin. N. Am.*, vol. 93, pp. 1373-1394 (2013).
A. Bertani, et al., International Society for Heart and Lung Transplantation, $32^{nd}$ Annual Meeting & Scientific Sessions, Poster No. 640, Apr. 18-12, 2012.
M. Struber, et al., *The Journal of Thoracic and Cardiovascular Surgery*, vol. 133, pp. 1620-1625 (2007).
M. Struber et al., The Journal of Thoracic and Cardiovascular Surgery, vol. 133, pp. 1620-1625 (2007).
A. Bertani et al., International Society for Heart and Lung Transplantation, $32^{nd}$ Annual Meeting, Apr. 18-21, 2012, Abstract No. 640 and attached poster.

* cited by examiner

*Primary Examiner* — Karen Cochrane Carlson
*Assistant Examiner* — Jennifer M. H. Tichy
(74) *Attorney, Agent, or Firm* — Oblon, McClelland, Maier & Neustadt, L.L.P.

(57) ABSTRACT

The present invention concerns a method of treating an advanced lung disease in a patient in need thereof by lung transplantation.

26 Claims, 2 Drawing Sheets

USE OF PULMONARY SURFACTANTS IN LUNG TRANSPLANTATION AND METHODS THEREOF

CROSS REFERENCES TO RELATED APPLICATIONS

This application claims priority to U.S. Provisional Patent Application No. 61/722,984, filed on Nov. 6, 2012, which is incorporated herein by reference in its entirety.

BACKGROUND OF THE INVENTION

1. Field of the Invention

The present invention relates to surgical procedures known as lung transplantation. In particular, the present invention relates to the use of an exogenous pulmonary surfactant for improving the clinical outcome of such a surgical procedure.

2. Discussion of the Background

Lung transplantation is a surgical procedure that should be considered for patients with advanced lung disease whose clinical status has progressively declined. Although successful lung transplantations were first performed in the 1980s, lung transplants have become widely used only as a result of a variety of improvements in the methodologies of such procedures. Thus improvements in, for example, donor management, donated lung preservation, immuno-suppression methods for preventing rejection of donated lungs by the lung transplant recipient, and infection-curing therapies for post-surgical recovery, have all contributed to a rise in the number of such transplantations performed worldwide.

Despite the general successfulness of lung transplantation methods, there is still a variety of serious and, in some cases, lethal consequences of these procedures such as for example ischemia/reperfusion (I/R) injury or even more severe consequences such as primary graft dysfunction and bronchiolitis obliterans syndrome (BOS).

In particular, since the I/R injury syndrome resembles very closely the ARDS syndrome, the administration of exogenous pulmonary surfactant during lung transplantation has been proposed. For instance, WO 2008/154151 discloses a method wherein the pulmonary surfactant is administered after the patient has received the lung transplant.

However, despite of the aforementioned improvements, there is still a need to develop more effective methods to prevent the adverse effects associated with lung transplantation.

Moreover, the widespread application of lung transplantation is limited by the shortage of suitable donor organs resulting in longer waiting times for listed patients with a substantial risk of dying prior to transplantation. Therefore, there is also a need of improved methods for the optimal utilization of the available donor lung pool.

These drawbacks have been mitigated by the method of the present invention that provides a real improvement over therapies described in the art.

SUMMARY OF THE INVENTION

Accordingly, it is one object of the present invention to provide novel lung transplantation methods.

It is another object of the present invention to provide novel methods of lung transplantation which mitigate the adverse effects associated with lung transplantation.

These and other objects, which will become apparent during the following detailed description, have been achieved by the inventors' discovery of a method of treating an advanced lung disease in a patient in need thereof by lung transplantation, said surgical procedure comprising the steps of:

(i) withdrawing a lung to be implanted from a donor and dissecting it on a backtable;

(ii) administering a therapeutically effective amount of an exogenous pulmonary surfactant directly into said lung on the back table after its withdrawal;

(iii) preserving said lung until implantation; and (iv) transplanting the lung into the patient (recipient).

In preferred embodiment, the lung preservation of step (iii) could be performed by applying the hypothermic (cold) static lung preservation technique or the ex vivo Lung Perfusion (EVLP) technique.

The present invention also contemplates a method of preserving a lung which will be implanted in a patient, said method comprising the step of administering a therapeutically effective amount of an exogenous pulmonary surfactant directly into said lung on the back table after its withdrawal.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
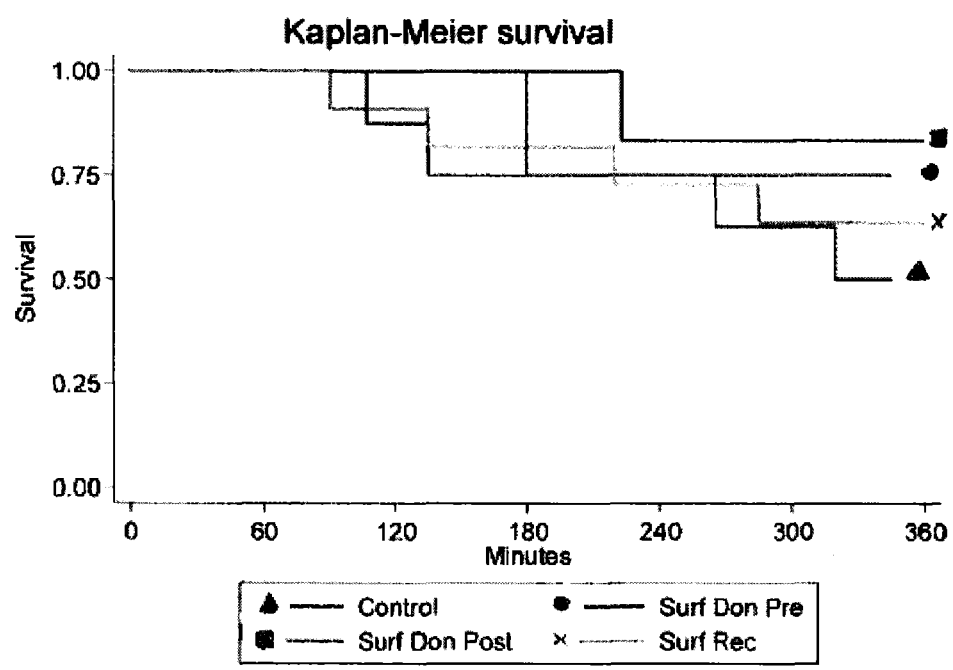
FIG. 1 shows the survival probability of treated animals in the four groups.

As used herein, the term "lung transplantation or transplant" refers to a surgical procedure in which a patient's diseased lungs are partially or totally replaced by lungs which come from a donor. The patient is also called recipient. The donor might be living or may have recently died or be brain dead, which means that although the donor's body is being kept alive by machines, the brain has no sign of life.

During the operation, the surgeon makes a cut in the chest and removes the diseased lung. The surgeon then sews the new lung to the main blood vessels and air passage.

Lung transplantation may be "single", in which just one of the two lungs is removed in the recipient and replaced with a single lung from the donor or "bilateral" which involves removing both lungs, one on each side and replacing both the lungs from the donor.

As used herein the expression "on the backtable" refers to the procedure performed on the lung that has been removed from a donor before it is replaced to a recipient on a sterile surgical table.

As used herein, the term "exogenous pulmonary surfactant" refers to any composition that acts to prevent lung collapse and includes modified natural pulmonary surfactants, reconstituted pulmonary surfactants, and artificial surfactants.

As used herein, the term "modified natural pulmonary surfactant" means a lipid extract of minced mammalian lung which, due to the lipid extraction step used in the manufacture process, is deprived of the hydrophilic proteins SP-A and SP-D and contains variable amounts of the hydrophobic proteins SP-B and SP-C. Depending on the method of extraction, the preparation may contain non-surfactant lipids and other components.

As used herein, the term "reconstituted pulmonary surfactant" means a synthetic composition made of a mixture of polar lipids, primarily phospholipids and optionally other components such as neutral lipids to which have been added surfactant proteins/peptides isolated from animals or proteins/peptides manufactured through recombinant technology such as those described in WO 95/32992, which is incorporated herein by reference in its entirety, or synthetic surfactant protein analogues such as those described in WO 89/06657, WO 92/22315, and WO 00/47623, all of three of which are incorporated herein by reference in their entireties.

As used herein, the term "artificial surfactant" means a synthetic composition made of simple mixtures of phospholipids and, optionally, other lipids, but devoid of surfactant proteins/peptides.

As used herein the term "lung preservation" refers to the process of maintaining and protecting a donor lung from the time of lung procurement up until implantation in the recipient has occurred.

As used herein, the term "ex vivo lung perfusion (EVLP)" refers to a lung preservation technique, in which the lung placed on a special perfusion rig whereby an artificial hyperoncotic solution with a hematocrit of 15%, now available commercially as Steen Solution™ (Vitrolife Inc., Englewood, Colo., USA), is pumped through the arteries of the lung whilst it is gradually rewarmed.

As used herein, the term "a therapeutically effective amount" is an amount that is sufficient to reduce the adverse effects associated to the lung transplantation.

As used herein, the expression "improving the clinical outcome" means an improvement statistically significant in terms of parameters such as survival and lung functionality.

Thus, the present invention is directed to a method of treating an advanced lung disease in a patient in need thereof by lung transplantation, said surgical procedure comprising the steps of:

(i) withdrawing a lung to be implanted from a donor and dissecting it on a back table;

(ii) administering a therapeutically effective amount of an exogenous pulmonary surfactant directly into said lung on the back table after its withdrawal;

(iii) preserving said lung until implantation; and (iv) transplanting the lung into the patient (recipient).

As reported in the Example below, it has been indeed found that the administration of the exogenous pulmonary surfactant directly into the lung being withdrawn from the donor, once on the back table, before preservation, can result in a significantly improved clinical outcome in terms of lung functionality and survival in comparison to is its administration through other modalities, i.e. before retrieval of the lung from the donor or after transplant to the patient.

The method of the present invention also allows an increase in the rate of organ usage from the donor pool.

The most common indications for lung transplantation include, but are not limited to, advanced chronic obstructive pulmonary disease (COPD), idiopathic pulmonary fibrosis (IPF), cystic fibrosis (CF), emphysema due to alpha-1 antitrypsin deficiency, and idiopathic pulmonary arterial hypertension (IPAH).

Steps (i) and (iv), including the selection of the potential donors and recipients, shall be carried out according to protocols and procedure known to the skilled person. Typical operations are described for instance in Example 1.

As far as step (ii) is concerned, any exogenous pulmonary surfactant currently in use, or hereafter developed for use in respiratory distress system and other pulmonary conditions, could be suitable for use in the present invention. These include modified natural, reconstituted, and artificial pulmonary surfactants.

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf™, Chiesi Farmaceutici SpA, Parma, Italy), and beractant (Survanta™, Abbott Laboratories, Inc., Abbott Park, Ill.)

Examples of reconstituted surfactants include, but are not limited to, lucinactant (Surfaxin™, Discovery Laboratories, Inc., Warrington, Pa.) and the product having the composition disclosed in WO 2010/139442, which is incorporated herein by reference in its entirety.

Examples of artificial surfactants include, but are not limited to, pumactant (Alec™, Britannia Pharmaceuticals, UK), and colfosceril palmitate (Exosurf™, GlaxoSmithKline, plc, Middlesex).

Preferably, the pulmonary surfactant is a modified natural surfactant or a reconstituted surfactant. More preferably the pulmonary surfactant is poractant alfa (Curosurf™).

Usually the pulmonary surfactant is administered as a suspension in a sterile pharmaceutically acceptable aqueous medium, preferably in a buffered physiological saline (0.9% w/v sodium chloride) aqueous solution.

Advantageously, the concentration of the surfactant might be from 5 to 160 mg/ml, preferably 25 to 100 mg/ml, more preferably from 30 to 80 mg/ml based on the total volume of the aqueous medium.

The dose of the pulmonary surfactant to be administered varies depending on the type of pulmonary surfactant and route of administration. Those skilled in the relevant art will be readily able to determine these factors and to adjust the dose accordingly.

For example, a dose may be used between of 10 and 200 mg/kg body weight, preferably between 25 and 80 mg/kg, body weight. In a preferred embodiment of the present invention, poractant alfa is administered at a dose of 30 mg/kg of body weight of the donor.

Advantageously, the pulmonary surfactant is administered in the trachea with or without the use of a bronchoscope.

As far as step (iii) is concerned, any lung preservation technique known by those skilled in the art may be used.

Parameters such as temperature, perfusion volume and pressure, oxygenation, and degree of inflation, that may impact the likelihood of lung injury during storage, shall be suitably adjusted by those skilled in the art.

In a preferred embodiment, the lung preservation of step (iii) could be performed by applying the hypothermic (cold) static lung preservation technique or the Ex vivo Lung Perfusion (EVLP) technique.

In cold static preservation, lungs are usually flushed with a Perfadex™ solution or another suitable solution known to the skilled person, and stored at 4° C. or 10° C., preferably 4°±1 C.

The conditions at which EVLP could be applied are known to the skilled person in the art, and for instance can be found in Cypel M., et al., The Journal of Heart and Lung Transplantation, December 2008, 1319-1325; or Cypel M., et al., Am J of Transplantation 2009, 9, 2262-2269, both of which are incorporated herein by reference in their entireties. Advantageously, it is carried out at a temperature of from 22 to 35° C., preferably at 32°±1 C Other features of the invention will become apparent in the course of the following descriptions of exemplary embodiments which are given for illustration of the invention and are not intended to be limiting thereof.

EXAMPLES

Example 1

Administration of Poractant Alfa (Curosurf™) in an Experimental Model of Ischemia/Reperfusion (I/R) in the Swine Under Different Conditions Animals.

64 Landrace white pigs were used for this study, weighting between 25 and 30 kg, in optimal general conditions. 32 male animals were used as donors and 32 female pigs as recipients of a left single lung transplant. The veterinary personnel performed a thorough clinical examination of all the animals before the surgical procedures. The animals were transferred to the appropriate pre-operative holding area two days before surgery for acclimatization.
Outline of the Study.
The animals were divided in 4 groups:
 1. Control (C): n=8, animals who received a single left lung transplant without any application of pulmonary surfactant.
 2. Group 1: n=8, animals who received a single left lung transplant and exogenous surfactant in the donor airway (surf don pre group).
 3. Group 2: n=8, animals who received a single left lung transplant and exogenous surfactant in the lung graft on the backtable, before storage (surf don post group).
 4. Group 3: n=8, animals who received a single left lung transplant and exogenous surfactant in the recipient after reperfusion of the graft (surf rec group).

Each experiment lasted for 2 days (day 1, procurement of the graft and 24 hours storage; day 2, lung transplantation and 6 hours observation period).

Exogenous surfactant was administered as follows at the dose of 30 mg/kg:
 Group 1: no administration
 Group 2: administration in the lung donor airway (via fiberoptic bronchoscope)
 Group 3: administration in the procured left lung on the backtable
 Group 4: administration in the lung recipient airway (via fiberoptic bronchoscope).
Anaesthesia.

All the animals, before anaesthesia induction, were given pre-medication with atropine (0.025 mg/kg s.c) and Zoletil 100 (5 mg/kg i.m.). The use of Zoletil (which is an exclusively veterinarian drug) for pre-medication, is required in order to reach an adequate sedation of the animal with a very low volume administration of i.m. drug (approximately 1.5 ml). The i.m. administration of drug was performed in the longissimus dorsi muscle, in the interscapular region.

After an adequate animal sedation was obtained, the animal was transferred to the cleaning area where it was completely cleansed and received a tricotomy. During this phase the peripheral oxygen saturation and the heart rate were monitored with a pulseoxymeter.

Induction of anesthesia was performed with Propofol (6 mg/kg) and Fentanyl (3 µg/kg) through a marginal ear vein and an 18 G venous cannula was placed. The animals, on spontaneous breathing, were intubated with a standard single-lumen endotracheal tube with the support of a standard straight or curved laryngoscope (Foregger, 22 cm). The animals were then mechanically ventilated on volume controlled ventilation with the following setting:
 PEEP=5 cmH$_2$O
 Tidal volume=10 ml/kg
 Respiratory rate=16 bpm
The FiO$_2$ was initially set at 50% and then adjusted based on the Arterial Blood Gas (ABG) results.

The anaesthesia maintenance protocol was similar in the different groups of the study.

A totally intra-venous anesthesia (TIVA) was performed with Propofol (100 mcg/kg/min), Ketanest (10 mg/kg/min) and Fentanyl (45 mcg/kg/h) in continuous infusion. At the beginning of the procedure, the maintenance drugs were given through the marginal vein of the ear. Following endotracheal intubation, a central venous access was obtained using a cut-down technique. Muscle paralysis was given as soon as a deep anesthesia status was reached. This initially consisted of Cisatracurium (nimbex) boluses (0.2 mg/kg), followed by a continuous infusion at the rate of 0.06 mg/kg/h. At the end of the procedure, the animal, under general anesthesia, was killed using a specific veterinary drug for euthanasia (Tanax 10 mg/kg).

In this study, the survival of the animal did not exceed the 6 hours of observation following the transplant and the reperfusion of the graft.

During the entire surgical procedure, a continuous i.v. drip was administered at the rate of 3 ml/h using either a crystalloid (D5 NS) or colloid solution (Voluven). The drip rate was adjusted according to blood loss and the hemodynamic status of the animal.
Intraoperative Monitoring.

A continuous intraoperative monitoring of vital signs was provided. During the phase of induction and the initial phase of the maintenance anaesthesia, the monitoring was non-invasive and included:
 Heart rate and continuous—5 lead—ECG
 Respiratory rate and ventilator parameters (airway peak pressure, tidal volume)
 Esophageal or rectal body temperature
 End Tidal CO$_2$ and SpO$_2$
 Non-invasive arterial pressure (q 30')

In the lung transplant recipients, after obtaining an adequate and stable maintenance anaesthesia, the following invasive measurements were obtained:
 Central venous pressure (via surgical isolation and cannulation of the left internal jugular vein)
 Systemic arterial pressure (via surgical isolation and cannulation of a branch of the left common carotid artery)
 Pulmonary pressures and wedge pressure (via Swan-Ganz catheter placed through the central venous line)
 Continuous hemodynamic monitoring (cardiac index, sVO$_2$, SVR) using a Vigilance device (Edwards, Critical Care).

The central venous access was also used to provide infusion of fluids, drugs, and to obtain venous blood samples. The arterial line also provided arterial blood samples for the maintenance of an adequate electrolyte balance, pH and gas exchange. The number and the type of samples to be obtained for the purpose of this study are described in the following section of this document. An adequate control of body temperature was provided by using thermostats beds.
Donor Operation.

The donor operation was performed on experiment day #1 and consisted of the en-block procurement of the heart-lung block and preparation of the left lung for 24 hours preservation and transplantation in the recipient animal on experiment day #2. The donors were male pigs weighting between 25 and 30 kg.

Operatory Steps:
  Median sternotomy
  Complete removal of the thymus
  Incision and opening of the pericardium and pleura
  Isolation of the Inferior Vena Cava (IVC), superior vena cava (SVC), and pulmonary arteria (PA)
  Administration of heparin (300 mg/kg) and placement of the pulmunoplegia cannula in the pulmonary artery
  Ligature of the SVC, section of the IVC, aortic crossclamp and incision of the left atrial appendage
  Administration of pulmunoplegia (Perfadex™, 1 L) and left atrial vent
  Topical cooling with cold (4° C.) saline and ice slush. Ventilation of the lungs with low tidal volumes (100 ml) and a respiratory rate of 5
  Removal of the heart-lung block in a semi-inflated state
  Cardiectomy and separation of the lungs. Preparation of the inflated left lung for storage in cold saline solution
  24 hours storage in cold saline solution at 4° C.

Recipient Operation.

Female pigs were used as recipients of left lung transplantation. The recipient weight was matched to the donor weight (approx. 25 to 30 kg). In case of a slight weight discrepancy, a recipient of lesser weight was preferred. Larger and heavier recipients were avoided to prevent downsizing of the donor lung.

Steps of the Operation:
  Supine position
  Isolation of the neck vessels with a cut-down technique and placement of a venous and arterial access, as previously described
  Fixation of the lines to the skin and closure of the neck incision
  Right lateral position (left side up)
  Full lateral thoracotomy in the 4th intercostal space and removal of the 5th rib
  Section of the pulmonary ligament
  Isolation of the left Azygos (Hemiazygos) vein, pulmonary artery, and pulmonary veins separately
  Dissection of the left atrium
  Isolation of the left main bronchus
  Ligation of the left main pulmonary artery and pulmonary veins. Left mainstream bronchus crossclamp
  Left pneumonectomy
  End to end bronchial anastomosis using 4-0 Prolene
  End to end atrial anastomosis using 5-0 Prolene
  Side to end arterial anastomosis using 5-0 Prolene
  Retrograde reperfusion and de-airing
  Anterograde reperfusion of the graft
  Crossclamp of the right mainstream bronchus and right pulmonary artery branches.

Postoperative Monitoring.

The ventilatory settings were kept stable during the entire experiment with the following settings:
  Volume controlled ventilation mode
  Tidal volume=8-10 ml/kg
  PEEP=5
  Respiratory rate=16

Based on the ABG samples, the haematocrit was kept stable and fluids were administered as required.

Every 30 minutes after the rap fusion of the graft the following measurements were performed:
  Cardiac output by means of the termodilution method
  Arterial blood gases
  Mean and peak airway pressures
  Systemic arterial pressure
  Pulmonary pressure Two hours after the reperfusion of the graft and at the end of the experiment a broncoalveolar lavage (BAL) in the left lower lobe bronchus was performed for the analysis of the pulmonary surfactant and the BAL cellular analysis. In addition, two tissue specimens were collected before and after reperfusion for histological analysis.

Variables of the Study.

The following variables underwent a statistical analysis:
  1. Survival of the animals
  2. Arterial blood gas parameters: pH, $PO_2/FIO_2$, $PCO_2$, BE, LACT, HT;
  3. Ventilation parameters: PIP, HR, VM, Vmpeso, PLAT_IP, Tvric_peso, PCWP, CO, CI, CVP, RVPI, ComTVPIP, $SPO_2$, MAP PAPm, MAP BP;
  4. BAL Parameters: total cells, cells/ml, retrieval %, vitality %, macrophages %, neutrophils %, lymphocytes %, eosinophils %.

Legend:
  $PO_2/FIO_2$: The ratio of partial pressure arterial oxygen and fraction of inspired oxygen
  $PCO_2$: partial pressure of carbon dioxide
  BE: base excess
  LACT: lactates
  HT: hematocrit
  PIP: peak inspiratory pressure
  HR: heart rate
  PLAT_IP: plateau inspiratory pressure
  PCWP: Pulmonary Capillary Wedge Pressure
  CO: cardiac output
  CI: cardiac index
  CVP: Central Venous Pressure
  RVPI: Indexed peripheral vascular resistance
  ComTVPIP: lung compliance
  $SPO_2$: Peripheral oxygen saturation
  MAP PAPm: mean arterial pulmonary pressure
  MAP BP: systemic mean arterial pressure
  BAL: broncho alveolar lavage.

Results.

In order to evaluate significant difference between groups, one way analysis of variance (ANOVA) was used.

Survival. Survival analysis refers to a number of techniques and statistical models used to describe and analyse a certain event (death or occurrence of disease, for example) in a sample group. The event must be precisely measurable in terms of time The "origin" time point usually refers to the moment when, for example, an individual is included into an experimental study. In this study, the origin time point is the time point referred to as Controlateral Clamp; at this time point the animal relies only on the new transplanted lung for survival.

The used survival function was the Kaplan-Meier.

The survival plots of the animals in the different groups are reported in FIG. 1. The results show that the animals in the Surf Don Post (3) group survive longer compared to controls. After 330 minutes, only 50% of the control animals survive compared to 83% of the animals in the Surf Don Post group.

The animals in the Surf Don Post (3) group also survive longer than both in the Surf Don Pre (2) group and in the Surf Rec (4) group.

The hemodynamic profile of the animals did not reveal profound differences in the different groups, although the untreated animals that had a worse survival actually died due to right heart failure and cardiocirculatory arrest.

Gas exchanges. Gas parameters, in particular in terms of $PO_2FIO_2$ (pO2/FiO2 ratio), were verified. The $PO_2/FiO_2$ ratio is an index to characterize the acute respiratory distress syndrome (ARDS), which involves severe hypoxemia (insufficient oxygen content in blood). PO2 is the partial pressure of oxygen in arterial blood. It is usually measured in millimeters of mercury (mmHg or Torr) by the test called arterial blood gas (ABG) analysis. FiO2 is the fraction of inspired oxygen or, simply percentage of oxygen, in a gas mixture.

The technique of Lowess (Locally Weighted Regression) Smoothing was used to elaborate the results. Said technique operates a weighted regression, at a local level, on the outcome variable over time: the concept of the Lowess technique is to create a new outcome variable that, for each observed value, contains a correspondent smoothed value. The action of smoothing, for every single observation point, is performed by considering the adjacent values, within a certain interval (bandwidth). In this study, a 0.8 bandwidth was used which means that 80% of the data was considered to smooth every single piece of data. This procedure, in general, generates a curve that follows the behaviour of the data and reduces the influence of possible outliers.

Figure 2:
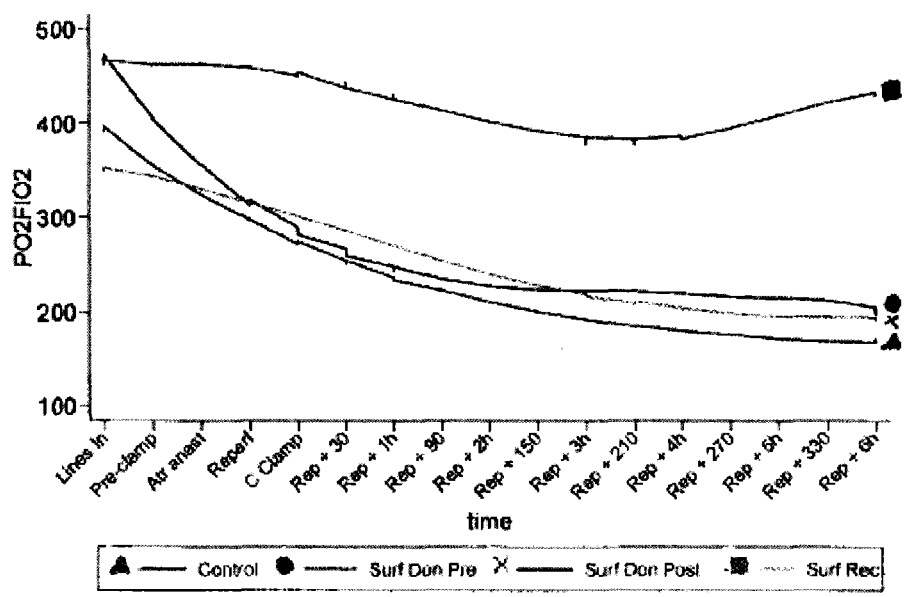
FIG. 2 shows the lowless of the variable PO2FIO2 ($pO_2$/$FiO_2$ ratio) in the four groups.

As it can be appreciated from FIG. 2, the $PO_2FIO_2$ in the Surf Don Post (3) group has higher values compared to the control group as well as the Surf Don Pre (2) group and in the Surf Rec (4) group, indicating that the lungs in the Surf Don Post (3) group exhibit a better oxygenation and hence an improved lung functionality.

Respiratory mechanics. It was evaluated in particular on the basis of the peak inspiratory pressure (PIP). The mean PIP value in the control group increases, while the PIP values in the Surf Don Pre (2), Surf Don Post (3) and Surf Rec (4) groups decrease indicating an improvement in the respiratory mechanics in all the treated groups. However, no significant difference was observed among the treated groups.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of treating an advanced lung disease selected from the group consisting of advanced chronic obstructive pulmonary disease (COPD), idiopathic pulmonary fibrosis (IPF), cystic fibrosis (CF), emphysema due to alpha-1 antitrypsin deficiency, and idiopathic pulmonary arterial hypertension (IPAH) in a patient in need thereof by lung transplantation, said method comprising:
   (i) withdrawing a lung with trachea to be implanted from a donor and dissecting it on a backtable;
   (ii) administering a therapeutically effective amount of an aqueous suspension of pulmonary surfactant poractant alfa having a concentration of 80 mg/ml based on the total volume of said aqueous suspension directly into the trachea on said back table after withdrawal of said lung;
   (iii) preserving said lung until implantation; and
   (iv) transplanting said lung into said patient,
   wherein said preserving said lung (iii) is carried out by applying a hypothermic (cold) static lung preservation technique.

2. A method according to claim 1, wherein said cold preservation technique is performed at a temperature of 4° C.

3. A method according to claim 1, wherein said poractant alfa is administered in an amount of 10 to 200 mg/kg of body weight of said donor.

4. A method according to claim 1, wherein said poractant alfa is administered in an amount of 25 to 80 mg/kg of body weight of said donor.

5. A method according to claim 1, wherein said poractant alfa is administered in an amount of 30 mg/kg of body weight of said donor.

6. A method according to claim 1, wherein said poractant alfa is administered into the trachea with a bronchoscope.

7. A method according to claim 1, wherein said poractant alfa is administered into the trachea without a bronchoscope.

8. A method according to claim 1, wherein said advanced lung disease is advanced chronic obstructive pulmonary disease (COPD).

9. A method according to claim 1, wherein said advanced lung disease is idiopathic pulmonary fibrosis (IPF).

10. A method according to claim 1, wherein said advanced lung disease is cystic fibrosis (CF).

11. A method according to claim 1, wherein said advanced lung disease is emphysema due to alpha-1 antitrypsin deficiency.

12. A method according to claim 1, wherein said advanced lung disease is idiopathic pulmonary arterial hypertension (IPAH).

13. A method according to claim 1, wherein said cold preservation technique is performed at a temperature of 4° C. or 10° C.

14. A method of treating an advanced lung disease selected from the group consisting of advanced chronic obstructive pulmonary disease (COPD), idiopathic pulmonary fibrosis (IPF), cystic fibrosis (CF), emphysema due to alpha-1 antitrypsin deficiency, and idiopathic pulmonary arterial hypertension (IPAH) in a patient in need thereof by lung transplantation, said method comprising:
   (i) withdrawing a lung with trachea to be implanted from a donor and dissecting it on a backtable;
   (ii) administering a therapeutically effective amount of an aqueous suspension of pulmonary surfactant poractant alfa having a concentration of 80 mg/ml based on the total volume of said aqueous suspension directly into the trachea on said back table after withdrawal of said lung;
   (iii) preserving said lung until implantation; and
   (iv) transplanting said lung into said patient,
   wherein said preserving said lung (iii) is carried out by applying a hypothermic (cold) static lung preservation technique without continuous perfusion and ventilation.

15. A method according to claim 14, wherein said cold preservation technique is performed at a temperature of 4° C.

16. A method according to claim 14, wherein said poractant alfa is administered in an amount of 10 to 200 mg/kg of body weight of said donor.

17. A method according to claim 14, wherein said poractant alfa is administered in an amount of 25 to 80 mg/kg of body weight of said donor.

18. A method according to claim 14, wherein said poractant alfa is administered in an amount of 30 mg/kg of body weight of said donor.

19. A method according to claim 14, wherein said poractant alfa is administered into the trachea with a bronchoscope.

20. A method according to claim 14, wherein said poractant alfa is administered into the trachea without a bronchoscope.

21. A method according to claim 14, wherein said advanced lung disease is advanced chronic obstructive pulmonary disease (COPD).

22. A method according to claim 14, wherein said advanced lung disease is idiopathic pulmonary fibrosis (IPF).

23. A method according to claim 14, wherein said advanced lung disease is cystic fibrosis (CF).

24. A method according to claim 14, wherein said advanced lung disease is emphysema due to alpha-1 antitrypsin deficiency.

25. A method according to claim 14, wherein said advanced lung disease is idiopathic pulmonary arterial hypertension (IPAH).

26. A method according to claim 14, wherein said cold preservation technique is performed at a temperature of 4° C. or 10° C.

* * * * *